US012178250B2

(12) United States Patent
Moloney

(10) Patent No.: US 12,178,250 B2
(45) Date of Patent: Dec. 31, 2024

(54) AEROSOL PROVISION SYSTEM AND A METHOD OF PROVIDING AN AEROSOL

(71) Applicant: Nicoventures Trading Limited, London (GB)

(72) Inventor: Patrick Moloney, London (GB)

(73) Assignee: NICOVENTURES TRADING LIMITED, London (GB)

( * ) Notice: Subject to any disclaimer, the term of this patent is extended or adjusted under 35 U.S.C. 154(b) by 501 days.

(21) Appl. No.: 17/600,590

(22) PCT Filed: Mar. 18, 2020

(86) PCT No.: PCT/GB2020/050702
§ 371 (c)(1),
(2) Date: Sep. 30, 2021

(87) PCT Pub. No.: WO2020/201701
PCT Pub. Date: Oct. 8, 2020

(65) Prior Publication Data
US 2022/0192266 A1    Jun. 23, 2022

(30) Foreign Application Priority Data
Apr. 5, 2019 (GB) .................................... 1904843

(51) Int. Cl.
*A24F 40/46* (2020.01)
*A24F 40/42* (2020.01)
*A24F 40/60* (2020.01)

(52) U.S. Cl.
CPC .............. *A24F 40/46* (2020.01); *A24F 40/42* (2020.01); *A24F 40/60* (2020.01)

(58) Field of Classification Search
None
See application file for complete search history.

(56) References Cited

U.S. PATENT DOCUMENTS 5,060,671 A * 10/1991 Counts .................... A24F 40/50
131/273
8,869,792 B1   10/2014 Lee
(Continued)

FOREIGN PATENT DOCUMENTS

CN    104886779 A    9/2015
EP    2782463 B1    6/2016
(Continued)

OTHER PUBLICATIONS

International Search Report and Written Opinion for International Application No. PCT/GB2020/050702, dated Jun. 19, 2020, 12 pages.
(Continued)

*Primary Examiner* — Tho D Ta
(74) *Attorney, Agent, or Firm* — Husch Blackwell

(57) ABSTRACT

There is provided an aerosol provision system comprising: aerosol generating medium; a source of energy for heating, wherein the source of energy for heating is configured to cause heating of the aerosol generating medium to form an aerosol; and a housing configured to house the aerosol generating medium and in which the source of energy for heating is located, the housing further comprising a protected region for protecting the heater; wherein the source of energy for heating is configured to move within the device between an aerosol generating position proximate to the aerosol generating medium and a stowed position in which the source of energy for heating is in the protected region.

24 Claims, 4 Drawing Sheets

(56) References Cited

U.S. PATENT DOCUMENTS

2014/0301721 A1　10/2014　Ruscio et al.
2015/0209530 A1　7/2015　White
2017/0055580 A1　3/2017　Blandino et al.

FOREIGN PATENT DOCUMENTS

| EP | 3610745 A1 | 2/2020 |
|----|---|---|
| RU | 2611487 C2 | 2/2017 |
| WO | 2013098395 A1 | 7/2013 |
| WO | 2015155289 A1 | 10/2015 |
| WO | 2016109932 A1 | 7/2016 |
| WO | 2017115196 A1 | 7/2017 |
| WO | WO 2018/190603 A1 | 10/2018 |

OTHER PUBLICATIONS

"International Preliminary Report on Patentability received for PCT Patent Application No. PCT/GB2020/050702, mailed on Oct. 14, 2021", 7 pages.
"Office Action and Search Report received for Russian Patent Application No. 2021128791, mailed on Mar. 31, 2022", 14 pages.
"Office Action received for Australian Patent Application No. 2020251738, mailed on Apr. 4, 2022", 3 pages.

\* cited by examiner

AEROSOL PROVISION SYSTEM AND A METHOD OF PROVIDING AN AEROSOL

CROSS-REFERENCE TO RELATED APPLICATIONS

This application is a National Phase entry of PCT Application No. PCT/GB2020/050702, filed Mar. 18, 2020, which application claims the benefit of priority to GB 1904843.8 filed Apr. 5, 2019, the entire disclosures of which are incorporated herein by reference.

TECHNICAL FILED

The present disclosure relates to an aerosol provision system, a method of generating an aerosol in an aerosol provision device, a consumable part for an aerosol provision device and an aerosol provision device.

BACKGROUND

Aerosol provision devices are known. Common devices use heaters to create an aerosol from a suitable medium which is then inhaled by a user. Often suitable media require significant levels of heating prior to generating an aerosol for inhalation. As such, the heaters of such devices reach high operational temperatures. User safety of such devices is important.

Various approaches are described herein which seek to help address or mitigate at least some of the issues discussed above.

SUMMARY

Aspects of the disclosure are defined in the accompanying claims.

In accordance with some embodiments described herein, there is provided an aerosol provision system comprising: aerosol generating medium; a source of energy for heating, wherein the source of energy for heating is configured to cause heating of the aerosol generating medium to form an aerosol; and a housing configured to house the aerosol generating medium and in which the source of energy for heating is located, the housing further comprising a protected region for protecting the heater; wherein the source of energy for heating is configured to move within the device between an aerosol generating position proximate to the aerosol generating medium and a stowed position in which the source of energy for heating is in the protected region.

In accordance with some embodiments described herein, there is provided a consumable part for the aerosol provision device.

In accordance with some embodiments described herein, there is provided a method of generating an aerosol in an aerosol provision device, the method comprising: providing aerosol generating medium; providing a source of energy for heating; providing a housing with a protected region; moving the source of energy for heating from a stowed position in which the source of energy for heating is located in the protected region to an aerosol generating position in which the source of energy for heating is located proximate to the aerosol generating medium; and, heating the aerosol generating medium to form an aerosol.

In accordance with some embodiments described herein, there is provided aerosol provision means comprising: aerosol generating means; a heating means, wherein the heating means is configured to cause heating of the aerosol generating means to form an aerosol; and a housing means configured to house the aerosol generating means and the heating means, the housing means further comprising a protecting means for protecting the heating means; wherein the heating means is configured to move within the device between an aerosol generating position proximate to the aerosol generating means and a stowed position in which the heating means is protected in the protected means.

In accordance with some embodiments described herein, there is provided an aerosol provision device configured to receive aerosol generating medium, comprising: a source of energy for heating, wherein the source of energy for heating is configured to, in use, heat the aerosol generating medium to form an aerosol; and a housing for housing, in use, the aerosol generating medium and in which the source of energy for heating is located, the housing further comprising a protected region for protecting the source of energy for heating; wherein the source of energy for heating is configured to, in use, move within the device between an aerosol generating position proximate to the aerosol generating medium and a stowed position in which the source of energy for heating is in the protected region.

DESCRIPTION OF DRAWINGS

The present teachings will now be described by way of example only with reference to the following figures in which like parts are depicted by like reference numerals.

Figure 1:
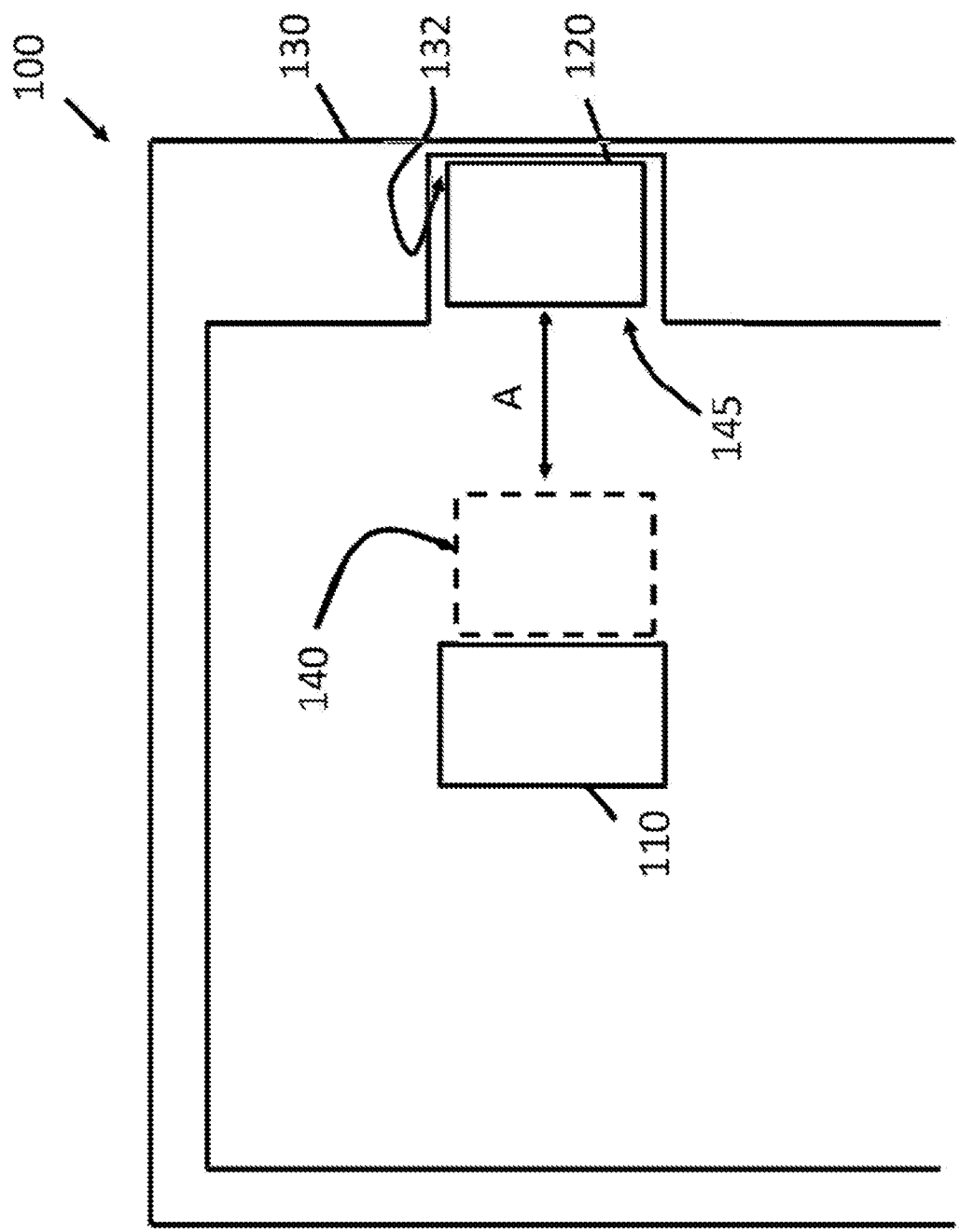
FIG. 1 is a schematic sectional view of a portion of an aerosol provision system according to an example.

While the invention is susceptible to various modifications and alternative forms, specific embodiments are shown by way of example in the drawings and are herein described in detail. It should be understood, however, that the drawings and detailed description of the specific embodiments are not intended to limit the invention to the particular forms disclosed. On the contrary, the invention covers all modifications, equivalents and alternatives falling within the scope of the present invention as defined by the appended claims.

DETAILED DESCRIPTION

Aspects and features of certain examples and embodiments are discussed/described herein. Some aspects and features of certain examples and embodiments may be implemented conventionally and these are not discussed/described in detail in the interests of brevity. It will thus be appreciated that aspects and features of apparatus and methods discussed herein which are not described in detail may be implemented in accordance with any conventional techniques for implementing such aspects and features.

The present disclosure relates to aerosol provision systems, which may also be referred to as aerosol provision systems, such as e-cigarettes. Throughout the following description the term "e-cigarette" or "electronic cigarette" may sometimes be used, but it will be appreciated this term may be used interchangeably with aerosol provision system/device and electronic aerosol provision system/device. Furthermore, and as is common in the technical field, the terms "aerosol" and "vapour", and related terms such as "vaporize", "volatilize", and "aerosolize", may generally be used interchangeably.

FIG. 1 illustrates a schematic view of a portion of an aerosol provision system 100 (sometimes herein referred to as an "aerosol provision device" or just "device"). The device 100 has a source of aerosol generating medium 110 within the device 100. The device 100 has a source of energy for heating 120 (sometimes herein referred to as a "heater") configured to heat the source of aerosol generating medium 110 to form an aerosol. The device 100 has a housing 130 configured to house the source of aerosol generating medium 110 and in which the heater 120 is located. The housing 130 comprises a protected region 132 for protecting the heater 120. The heater 120 is configured to move within the device 100 between an aerosol generating position 140 proximate to the source of aerosol generating medium 110 and a stowed position 145 in which the heater 120 is in the protected region 132.

The "protected" region 132 as used herein means a region within the device 100 which is generally protected in some way such as sheltered, covered, difficult to access or the like. When the heater 120 is in the protected region 132, the heater 120 is difficult to be contacted by a user, and the heater 120 is considered to be in the stowed position 145. In devices 100 where the user replaces the source of aerosol generating medium 110 by, for example, opening the device 100, there is a danger that the user may contact components in the device 100 which may then be damaged by such contact. Similarly, if the heater 120 is hot and the user accesses the inner of the device 100 there is a danger the user may injure themselves. As such, moving the heater 120 into a protected region 132 when not in use reduces the likelihood of the user injuring themselves and similarly increases the lifetime of the device 100. The protected region 132 may be located between 0.5 cm to 2.0 cm from the aerosol generating position 140. In an example, the protected region 132 is located about 1.0 cm from the aerosol generating position 140.

As shown in FIG. 1, the heater 120 may move along a direction shown by arrow A between the stowed position 145 and the aerosol generating position 140. The heater 120 may move in one direction towards the source of aerosol generating medium 110 and the aerosol generating position 140 or in more than one direction. One direction of movement of the heater 120 may benefit from being fairly mechanically simple to achieve. This reduces the cost of the device 100 as a whole. More than one direction of movement may be mechanically more complex to deliver however this reduces the likelihood of the source of aerosol generating medium 110 or aerosol or aerosol entering the protected region 132. It can clearly be understood that if the heater 120 is moved along a convoluted path to reach the aerosol generating position 140, it is unlikely the source of aerosol generating medium 110 will, for example if dislodged during transit, be able to fall into the protected region 132.

The movement of the heater 120 may be provided by a motor or a resilient member arrangement which may operate with a lever to bias the heater 120 into either the stowed position 145 or the aerosol generating position 140. In an example, the resilient member biases the heater 120 into the protected region 132 and the lever, when activated, can operate against the bias to push the heater 120 to the aerosol generating position. The heater 120 may be on a shaft that is projected towards the aerosol generating position 140, during use of the device 100, and retracted to the stowed position 145, after use, by the action of an associated motor or the like. The device 100 may comprise cams or a Geneva wheel or the like for moving the heater 120.

The heater 120 may be moved deeper into the device 100. "Deeper" here is intended to mean further into the device 100 from the outer edges of the housing 130. The movement deeper into the device 100 prevents the heat generated from the heater 120 being transmitted to the surfaces of the device 100 which may contact, or be contacted by, a user. This therefore increases the safety of the device 100. Such an arrangement is particular advantageous in the event of a high thermal capacity heater, which will continue to produce heat after the smoking session has concluded. This arrangement may shield a user from heater 120 burns via contact through the outer surface of the housing 130.

During periods of non-operation of the device 100, the heater 120 may be maintained in the stowed position 145. The protected region 132 may be, as shown in FIG. 1, at least one of a recess, opening, corridor, through-hole, groove or cavity within the housing 130 of the device 100. The stowed position 145, which is the position the heater 120 takes when in the protected region 132, may be located between two sections of housing 130 of the device 100. The stowed position 145 is a protected position, by virtue of being in the protected region 132, within the device 100 which may protect the heater 120 from, for example, being damaged during transit of the device 100.

The protection may be provided by elements or features of the housing of the device 100 as shown in FIG. 1. The protection may be provided by sheltering or covering the heater 120 in some manner, for example by covering a majority of the heater 120. There may be only one route into and out of the protected region 132 along the axis of movement of the heater 120. In another arrangement (not shown), the device 100 may have a door or cover which is closable when the heater 120 is in the protected region 132 so as to provide a full covering of the heater 120. The door may automatically close over the entrance to the protected region 132 when the heater 120 is moved into the stowed position 145 through the entrance to the stowed position 145. The housing 130 of the device 100 may have a protecting structure in which the protected region 132 is located. This structure could be for example a plate or a block or side walls or the like into which the heater 120 can retract rather than retracting into the whole housing 130 itself.

The aerosol generating position 140, shown by a position marked out by a dashed line in FIG. 1, is a position wherein the heater 120 is able to heat the source of aerosol generating medium 110. The heater 120 and source of aerosol generating medium 110 may be proximal, adjacent or abutting when the heater 120 is in the aerosol generating position 140. The source of aerosol generating medium 110 may be arranged downstream of the heater 120 so that aerosol generated as a result of the heater 120 heating the source of aerosol generating medium 110 flows away from the heater 120. This arrangement reduces the likelihood of aerosol condensing on the heater 120 and therefore increases the cleanliness of operation of the device 100. In turn, this increases the lifetime of the heater 120 and therefore reduces the cost of maintenance of the device 100.

The heater 120 may be moved into the aerosol generating position 140 prior to or on initiation of a smoking session. The movement of the heater 120 may be automated or may occur on user request. The automation of the movement of the heater 120 may be achieved using, for example, a puff detector. Upon detection of a puff by the user, the heater 120 may be moved from the stowed position 145 to the aerosol generating position 140. The device 100 may have detectors or sensors located in, for example, the mouthpiece of the device 100 such that when the user places the device 100 in their mouth, the heater 120 is moved from the stowed position 145 to the aerosol generating position 140. Alternatively, the mouthpiece could be movable so as to affect movement in the heater 120. The mouthpiece may have an element, such as a biased member, such as a tensioned spring, which is affected by placement of the mouthpiece into the user's mouth which provides movement, directly or indirectly, to the heater 120. The mouthpiece and housing 130 of the device 100 may be slidably moveable in relation to one another, such that movement of the mouthpiece directly moves the heater 120 to the aerosol generating position 140. The device 100 may alternatively or additionally have a button, or the like, which a user may press to instruct the movement of the heater 120 from the stowed position 145 to the aerosol generating position 140. Activation of the heater 120 may occur prior to, in tandem with, or with a delay from, the movement of the heater 120.

Figure 2:
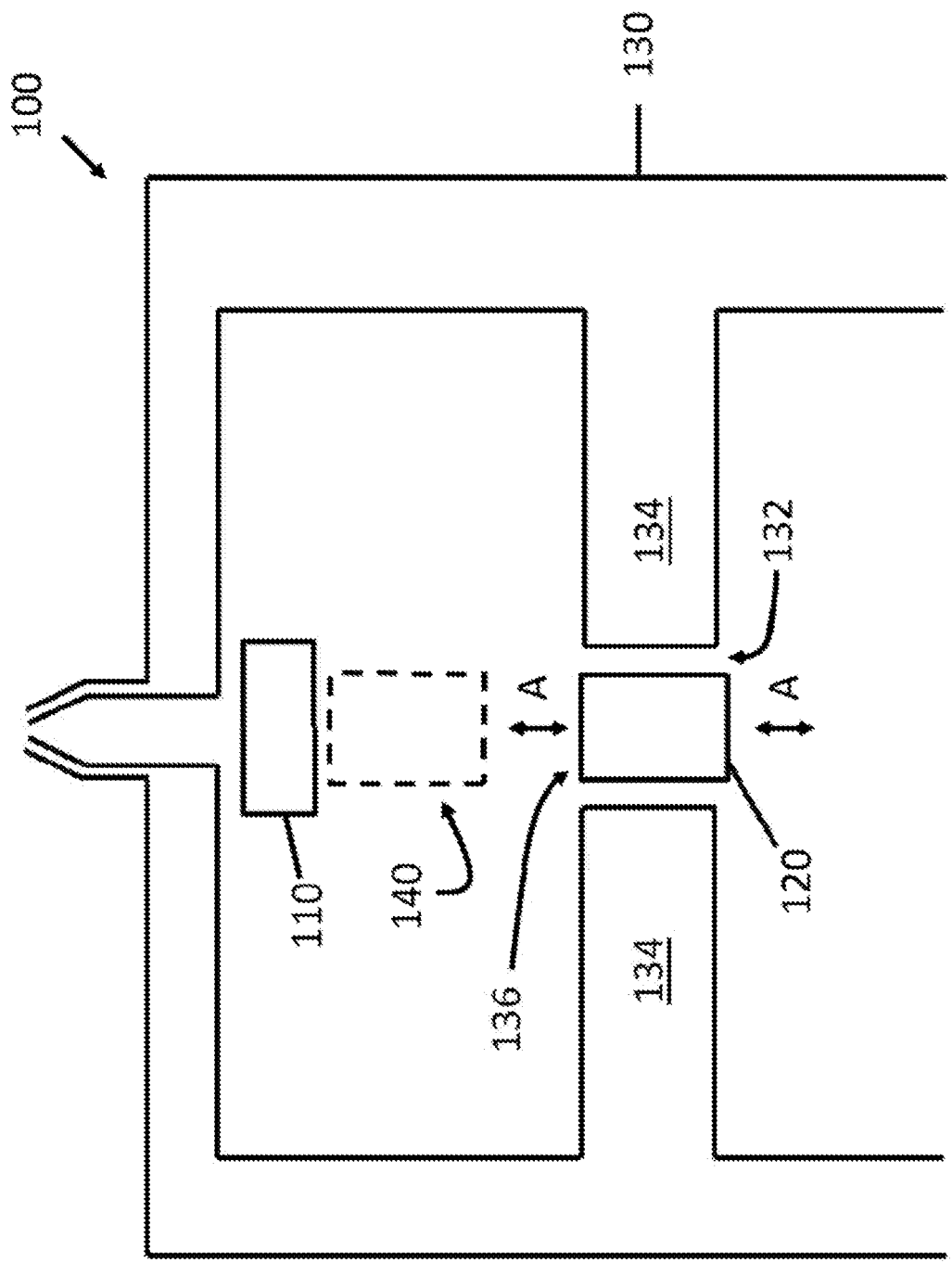
FIG. 2 is a schematic sectional view of a portion of an aerosol provision system according to an example.

FIG. 2 illustrates a schematic view of a portion of an aerosol provision device 100. Reference numerals indicating the same features as shown in FIG. 1 are the same as those numerals used in FIG. 1. These same features will not be discussed in detail here. The protected region 132 shown in FIG. 2 is arranged between two elements 134 of the housing. The elements 134 in the example of FIG. 2 are projecting elements 134. The projecting elements 134 project from either side of the housing 130 towards a central position. The projecting elements 134 are positioned to leave a protected region 132 between the ends of the two projecting elements 134 in which the heater 120 is shown. The heater 120 can be moved from, and retracted into, this protected region 132 in the directions indicated by the arrows A.

The shape of the source of aerosol generating medium 110 is such that the source of aerosol generating medium 110 is prevented from entering the protected region 132. Preventing the source of aerosol generating medium 110 from entering the protected region 132 can increase the cleanliness of the device 100. If the source of aerosol generating medium 110 enters the protected region it may get burned from being to close to the heater 120 for too long a time. This can result is an undesirable user experience. In another example, the device 100 has a preventing object arranged to prevent the aerosol generating medium 110 from entering the protected region 132. The preventing object may be a block, a bar, a grill, a mesh or the like.

In an example, the protected region 132 has an entrance 136 through which the heater 120 is arranged to move as the heater 120 moves from the aerosol generating position 140 to the stowed position 145. This entrance 136 may have an area of less than 1.5 cm², less than 1.2 cm² or less than 1.0 cm². In an example, the entrance 136 has a 12 mm by 12 mm square opening. In this way, the source of aerosol generating medium 110 may be sized so as to be prevented from entering the protected region 132. In another example, the entrance 136 has a smallest dimension of 12 mm or less. In an example, the entrance 136 has an area of $\pi*(6 \text{ mm})^2$ or less, where the radius of the entrance is 6 mm and the entrance is substantially circular.

As can be seen in the example shown in FIG. 2, the source of aerosol generating medium 110 has a width greater in size than the entrance 136 of the protected region 132. The source of aerosol generating medium 110 may have a base which is sized to be too large to fit into the protected region 132. In an example, the distance between the protected region 132 and the aerosol generating position 140 may be a length that is about equal to half the max linear distance across the area of the entrance 136.

Figure 3:
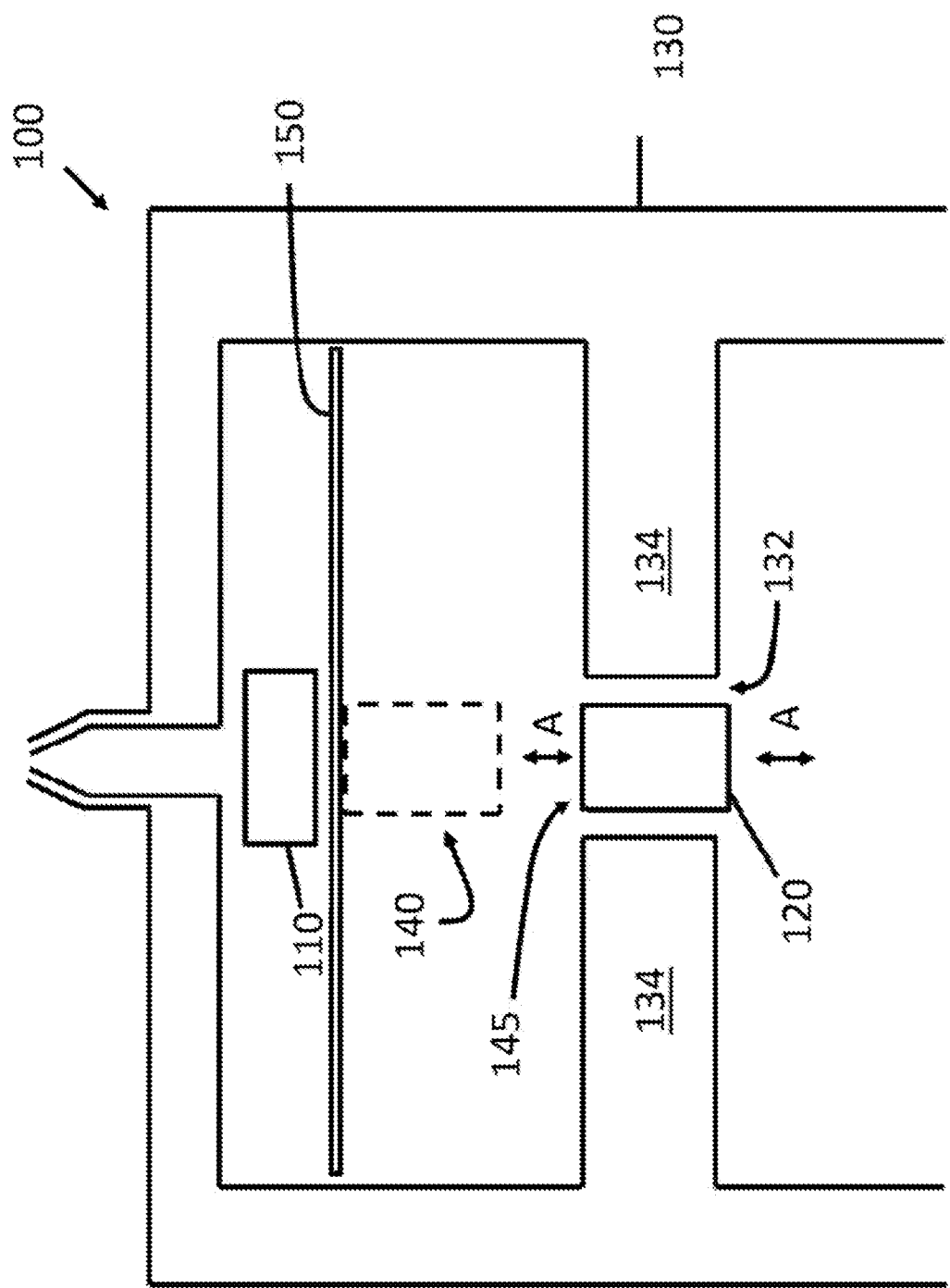
FIG. 3 is a schematic sectional view of a portion of an aerosol provision system according to an example; and, FIG. 4 shows schematic views of an aerosol provision system in various stages of use according to an example.

FIG. 3 shows a schematic sectional view of a portion of an aerosol provision device 100 according to an example. Reference numerals indicating the same features as shown in FIG. 1 or 2 are the same as those numerals used in FIG. 1 or 2. These same features will not be discussed in detail here. The device 100 shown in FIG. 3 has a further element 150 which can prevent the source of aerosol generating medium 110 from entering the protected region 132. Moreover, this element 150 is positioned between the aerosol generating position 140 and the source of aerosol generating medium 110 and, as such, the source of aerosol generating medium 110 is substantially prevented from moving near to the heater 120. The heater 120 and source of aerosol generating medium 110 only become close to one another as the heater 120 moves from the stowed position 145 to the aerosol generating position 140. In this way, heating of the source of aerosol generating medium 110 can be easily controlled and the risk of heating of the source of aerosol generating medium 110 prior to the designated heating session is significantly reduced.

Furthermore, the element 150 may further protect the heater 120 from being contacted as a user accesses the device 100 to remove or replace the source of aerosol generating medium 110. The element 150 may be a netting, or a fence-like structure, which is made from thermally conductive material. In this example, the heat conductive netting 150 would prevent movement of the source of aerosol generating medium 110 while allowing thermal energy to pass from the heater 120 to the source of aerosol generating medium 110. The netting 150 may be made of wire mesh or a metal linking or the like. Functionally, the element 150 enables thermal energy to pass while preventing sizeable structural elements from passing.

Figure 4:
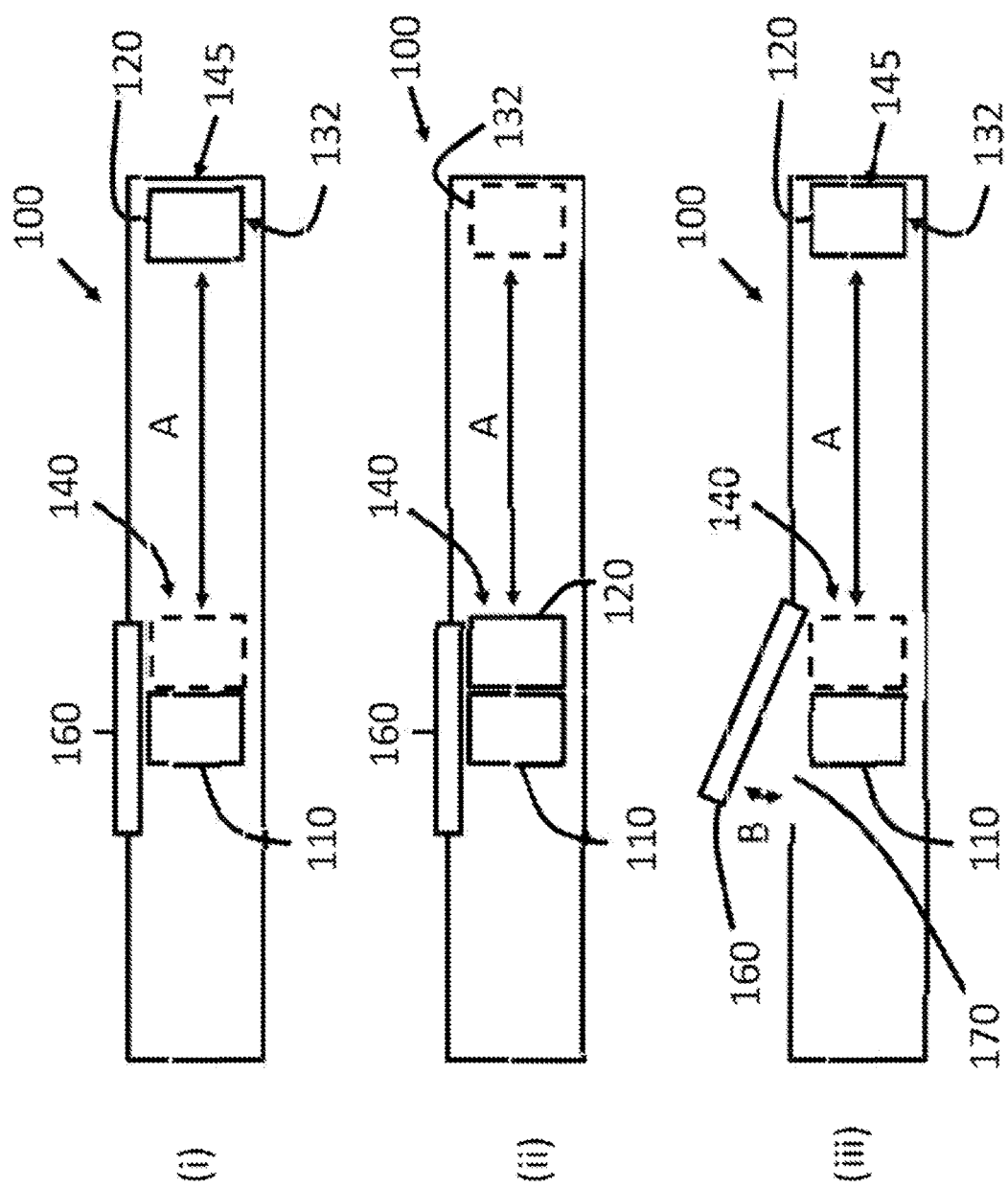

FIG. 4 shows three schematic views of an aerosol provision device 100 in various stages of use according to an example. Reference numerals indicating the same features as shown in FIG. 1, 2 or 3 are the same as those numerals used in FIG. 1, 2 or 3. FIG. 4(*i*) shows the device 100 at rest, when not in use to produce an aerosol. The heater 120 is located in the protected region 132. The protected region 132 may be a groove or the like as described above, though this is not explicitly shown in FIG. 4. The source of aerosol generating medium 110 is located a distance away from the heater 120. The heater 120 is movable to, and from, the aerosol generating position 140 along the direction indicated by arrow A. The device 100 has a cover 160 for covering a cover opening 170 (see FIG. 4(*iii*)) to the device 100. The cover 160 is configured to move between a closed position for covering the opening (see FIG. 4(*i*)) and an open position for providing a user access to the device 100 through the cover opening 170 (see FIG. 4(*iii*)). The device 100 is arranged so that the heater 120 is in the stowed position 145 as the cover 160 is moved towards the open position.

As a heating session is initiated, the cover is already closed 160 and the heater 120 moves to the aerosol generating position 140 as shown in FIG. 4(*ii*). After the heating session is completed, the heater 120 moves to the stowed position 145 and the cover 160 may be moved to the open position by movement in a direction indicated by one end of the arrow B. Moving the cover 160 from covering the cover opening 170 enables the user to access the inside of the device 100. The cover 160 can be closed by moving the cover 160 along the other direction indicated by the other end of the arrow B. The movement of the cover 160 is shown as a rotating motion in FIG. 4.

The cover 160 may be a door or hatch or the like, which may rotate to the open position or may slide to the open position or the like. The cover 160 may be fully removable from the device 100. The source of aerosol generating medium 110 is shown in FIG. 4 to be located near the cover 160. This increases the ease with which the user may remove the source of aerosol generating medium 110 from the device 100. The cover 160 may have a lock to prevent access to the inside of the device 100 when the heater 120 is in the aerosol generating position 140. The lock may be automatically activated by the heater 120 moving to the aerosol generating position 140. There may be a feedback system in the device 100 such that the device 100 cannot be activated when the cover 160 is in the open position. These safety measures reduce the risk of the user contacting a hot heater 120 while accessing the inside of the device 100.

In some instances, such as maintenance or troubleshooting of the device 100, the cover 160 may need to be in the open position while the heater 120 is in the aerosol generating position 140. The device 100 may comprise an override system to enable the cover 160 to be in the open position and the heater 120 to be in the aerosol generating position 140 simultaneously. The override system may be activatable by a designated operator. The override system may be activated by a code or a key or the like known only to the designated operator. This would allow for example maintenance of the heater 120 by a professional. The heater 120 may be of a size to pass through the cover opening 170 to enable removal or replacement or maintenance of the heater 120.

In an example, the device 100 may be constructed so that the protected region 132 is arranged substantially more centrally within the housing 130 than the aerosol generating position 140. This may be because the aerosol generating position 140 is located closer to a mouthpiece of the device 100 so that when aerosol is generated it has a reduced distance to flow within the device 100 prior to exiting the device 100, through for example, a mouthpiece or outlet. This reduces the area within the device 100 on which the aerosol may condense. Reduction of the flow path of the generated aerosol reduces the number of components within the device 100 on which the generated aerosol can condense. Aerosol that condenses within the device 100 may damage these components. Therefore, an arrangement wherein the protected region 132 is arranged substantially more centrally within the housing 130 than the aerosol generating position 140 may lead to a prolonged lifetime of the device 100 as well as increased cleanliness of the device 100.

Such an arrangement also reduces the amount of heat energy that is generated by the device 100 near an outer surface of the device 100 on which the user may grip the device 100. As such, it reduces the danger of a user being injured by holding a hot housing 130 of the device 100. The heater 120 may be deactivated prior to moving to the stowed position 145 however, in this arrangement, latent heat within the heater 120 is prevented from easily heating the surface of the device 100 via heating the housing 130.

In an example, the heater 120 may be activated prior to movement along the axis shown by arrow A in FIG. 4(i). This activation may occur in response to detection by a puff sensor of initiation of a smoking session or activation of a user-activatable button, as described above. To provide the user with minimal wait time prior to aerosol being generated, the heater 120 should be as close to operational temperatures when the source of aerosol generating medium 110 and the heater 120 come together. As such, the heater 120 may be heated during movement or prior to movement of the source of aerosol generating medium 110 or the heater 120. The device 100 may have a controller to control movement and heating phases, to maximise user experience.

The device 100 may have a movement mechanism for moving the heater 120. The movement mechanism for the heater 120 may be located in a position which is near both the stowed position 145 and the aerosol generating position 140. In an example, the movement mechanism may be positioned in the protected region 132. In another example, the movement mechanism may be positioned near the aerosol generating position 140. The movement mechanism may be arranged on the axis as shown by the arrow A in FIG. 4. For example, the movement mechanism may be arranged on an opposite side of the heater 120 to the aerosol generating position 140 along the axis shown by arrow A.

The source of aerosol generating medium 110 may comprise a single dose of aerosol generating material or a number of separate doses of aerosol generating material. In implementations with a plurality of doses, each dose may be separately heatable to produce a predetermined amount of aerosol per use. The doses may be arranged on a base or substrate of the source of aerosol generating medium 110 so as to be individual and separate within or on the source of aerosol generating medium 110 or may overlap or be adjacent (i.e. the different does may comprise different areas of a single region of aerosol generating material).

The source of aerosol generating medium 110 may take any suitable form or construction. In one embodiment, the source of aerosol generating medium may include a substrate (for example, paper, card, foil) including a first and second side, with the aerosol generating medium disposed on the first side of the substrate. The substrate in this instance may act as a carrier for the aerosol generating medium. In some implementations, the substrate may be, or may include, a metallic element that is arranged to be heated by a varying magnetic field. In such implementations, the source of energy for heating 120 may include an induction coil, which, when energised, causes heating within the metallic element of the source 110. The degree of heating may be affected by the distance between the metallic element and the induction coil. In yet further alternative implementations, the source of aerosol generating medium 110 may consist entirely (or substantially entirely) of aerosol generating medium (i.e., without a carrier). For the purposes of describing a concrete example, the source 110 described herein includes a substrate with aerosol generating medium disposed on the first side of the substrate, while the source of energy for heating 120 is herein a resistive heater.

The substrate may be impermeable to aerosol or may be porous such that the aerosol generating medium may be located in the pores of the substrate. In an example, the substrate may have permeable and impermeable portions. Permeable portions may be located in portions wherein it is desirable to have aerosol pass through the substrate, such as to allow flow through the substrate and towards the outlet of the device 100. Impermeable portions may be located in portions wherein it is desirable to prevent aerosol flowing towards the source of energy for heating 120.

Each of the plurality of doses may be separately heatable by relative movement between the heater 120 and the doses of aerosol generating material to align different doses with the heater 120 at different times. The source of aerosol generating medium 110 may therefore move independently of the heater 120. The source of aerosol generating medium 110 may rotate about a central axis to present a different portion of the source of aerosol generating medium 110 to the heater 120. This may correspond to different doses of the source of aerosol generating medium 110 being heated, which may correspond to different aerosol generating media, such as tobacco or menthol or the like. This enables the device 100 to provide a number of different user experiences. The source of aerosol generating medium 110 may be moved by any of the methods or components described herein in relation to movement of the heater 120.

The source of aerosol generating medium 110 or the doses contained within the source of aerosol generating medium 110 may comprise at least one of tobacco and glycol and may include extracts (e.g., licorice, hydrangea, Japanese white bark magnolia leaf, chamomile, fenugreek, clove, menthol, Japanese mint, aniseed, cinnamon, herb, wintergreen, cherry, berry, peach, apple, Drambuie, bourbon, scotch, whiskey, spearmint, peppermint, lavender, cardamon, celery, cascarilla, nutmeg, sandalwood, bergamot, geranium, honey essence, rose oil, vanilla, lemon oil, orange oil, cassia, caraway, cognac, jasmine, ylang-ylang, sage, fennel, piment, ginger, anise, coriander, coffee, or a mint oil from any species of the genus *Mentha*), flavour enhancers, bitterness receptor site blockers, sensorial receptor site activators or stimulators, sugars or sugar substitutes (e.g., sucralose, acesulfame potassium, aspartame, saccharine, cyclamates, lactose, sucrose, glucose, fructose, sorbitol, or mannitol), and other additives such as charcoal, chlorophyll, minerals, botanicals, or breath freshening agents. They may be imitation, synthetic or natural ingredients or blends thereof. They may be in any suitable form, for example, oil, liquid, or powder. The doses may be separated, adjacent or overlapping.

The aerosol-forming layer described herein comprises an "amorphous solid", which may alternatively be referred to as a "monolithic solid" (i.e. non-fibrous), or as a "dried gel". The amorphous solid is a solid material that may retain some fluid, such as liquid, within it. In some cases, the aerosol-forming layer comprises from about 50 wt %, 60 wt % or 70 wt % of amorphous solid, to about 90 wt %, 95 wt % or 100 wt % of amorphous solid. In some cases, the aerosol-forming layer consists of amorphous solid.

In some cases, the amorphous solid may comprise 1-50 wt % of a gelling agent wherein these weights are calculated on a dry weight basis.

Suitably, the amorphous solid may comprise from about 1 wt %, 5 wt %, 10 wt %, 15 wt %, 20 wt % or 25 wt % to about 50 wt %, 45 wt %, 40 wt %, 35 wt %, 30 wt % or 27 wt % of a gelling agent (all calculated on a dry weight basis). For example, the amorphous solid may comprise 5-40 wt %, 10-30 wt % or 15-27 wt % of a gelling agent.

In some embodiments, the gelling agent comprises a hydrocolloid. In some embodiments, the gelling agent comprises one or more compounds selected from the group comprising alginates, pectins, starches (and derivatives), celluloses (and derivatives), gums, silica or silicones compounds, clays, polyvinyl alcohol and combinations thereof. For example, in some embodiments, the gelling agent comprises one or more of alginates, pectins, hydroxyethyl cellulose, hydroxypropyl cellulose, carboxymethylcellulose, pullulan, xanthan gum guar gum, carrageenan, agarose, acacia gum, fumed silica, PDMS, sodium silicate, kaolin and polyvinyl alcohol. In some cases, the gelling agent comprises alginate or pectin, and may be combined with a setting agent (such as a calcium source) during formation of the amorphous solid. In some cases, the amorphous solid may comprise a calcium-crosslinked alginate or a calcium-crosslinked pectin.

Suitably, the amorphous solid may comprise from about 5 wt %, 10 wt %, 15 wt %, or 20 wt % to about 80 wt %, 70 wt %, 60 wt %, 55 wt %, 50 wt %, 45 wt % 40 wt %, or 35 wt % of an aerosol generating agent (all calculated on a dry weight basis). The aerosol generating agent may act as a plasticiser. For example, the amorphous solid may comprise 10-60 wt %, 15-50 wt % or 20-40 wt % of an aerosol generating agent. In some cases, the aerosol generating agent comprises one or more compound selected from erythritol, propylene glycol, glycerol, triacetin, sorbitol and xylitol. In some cases, the aerosol generating agent comprises, consists essentially of or consists of glycerol. The inventors have established that if the content of the plasticiser is too high, the amorphous solid may absorb water resulting in a material that does not create an appropriate consumption experience in use. The inventors have established that if the plasticiser content is too low, the amorphous solid may be brittle and easily broken. The plasticiser content specified herein provides an amorphous solid flexibility which allows the amorphous solid sheet to be wound onto a bobbin, which is useful in manufacture of aerosol generating articles.

In some cases, the amorphous solid may comprise a flavour. Suitably, the amorphous solid may comprise up to about 60 wt %, 50 wt %, 40 wt %, 30 wt %, 20 wt %, 10 wt % or 5 wt % of a flavour. In some cases, the amorphous solid may comprise at least about 0.5 wt %, 1 wt %, 2 wt %, 5 wt % 10 wt %, 20 wt % or 30 wt % of a flavour (all calculated on a dry weight basis). For example, the amorphous solid may comprise 10-60 wt %, 20-50 wt % or 30-40 wt % of a flavour. In some cases, the flavour (if present) comprises, consists essentially of or consists of menthol. In some cases, the amorphous solid does not comprise a flavour.

In some cases, the amorphous solid additionally comprises a tobacco material or nicotine. For example, the amorphous solid may additionally comprise powdered tobacco or nicotine or a tobacco extract. In some cases, the amorphous solid may comprise from about 1 wt %, 5 wt %, 10 wt %, 15 wt %, 20 wt % or 25 wt % to about 70 wt %, 60 wt %, 50 wt %, 45 wt % or 40 wt % (calculated on a dry weight basis) of a tobacco material or nicotine.

In some cases, the amorphous solid comprises a tobacco extract. In some cases, the amorphous solid may comprise 5-60 wt % (calculated on a dry weight basis) of tobacco extract. In some cases, the amorphous solid may comprise from about 5 wt %, 10 wt %, 15 wt %, 20 wt % or 25 wt % to about 55 wt %, 50 wt %, 45 wt % or 40 wt % (calculated on a dry weight basis) tobacco extract. For example, the amorphous solid may comprise 5-60 wt %, 10-55 wt % or 25-55 wt % of tobacco extract. The tobacco extract may contain nicotine at a concentration such that the amorphous solid comprises 1 wt % 1.5 wt %, 2 wt % or 2.5 wt % to about 6 wt %, 5 wt %, 4.5 wt % or 4 wt % (calculated on a dry weight basis) of nicotine. In some cases, there may be no nicotine in the amorphous solid other than that which results from the tobacco extract.

In some embodiments the amorphous solid comprises no tobacco material but does comprise nicotine. In some such cases, the amorphous solid may comprise from about 1 wt %, 2 wt %, 3 wt % or 4 wt % to about 20 wt %, 15 wt %, 10 wt % or 5 wt % (calculated on a dry weight basis) of nicotine. For example, the amorphous solid may comprise 1-20 wt % or 2-5 wt % of nicotine.

In some cases, the total content of tobacco material, nicotine and flavour may be at least about 1 wt %, 5 wt %, 10 wt %, 20 wt %, 25 wt % or 30 wt %. In some cases, the total content of tobacco material, nicotine and flavour may be less than about 70 wt %, 60 wt %, 50 wt % or 40 wt % (all calculated on a dry weight basis).

In some embodiments, the amorphous solid is a hydrogel and comprises less than about 20 wt % of water calculated on a wet weight basis. In some cases, the hydrogel may comprise less than about 15 wt %, 12 wt % or 10 wt % of water calculated on a wet weight basis (WWB). In some cases, the hydrogel may comprise at least about 2 wt % or at least about 5 wt % of water (WWB).

The amorphous solid may be made from a gel, and this gel may additionally comprise a solvent, included at 0.1-50 wt %. However, the inventors have established that the inclusion of a solvent in which the flavour is soluble may reduce the gel stability and the flavour may crystallise out of the gel. As such, in some cases, the gel does not include a solvent in which the flavour is soluble.

The amorphous solid comprises less than 20 wt %, suitably less than 10 wt % or less than 5 wt % of a filler. The filler may comprise one or more inorganic filler materials, such as calcium carbonate, perlite, vermiculite, diatomaceous earth, colloidal silica, magnesium oxide, magnesium sulphate, magnesium carbonate, and suitable inorganic sorbents, such as molecular sieves. The filler may comprise one or more organic filler materials such as wood pulp, cellulose and cellulose derivatives. In some cases, the amorphous solid comprises less than 1 wt % of a filler, and in some cases, comprises no filler. In particular, in some cases, the amorphous solid comprises no calcium carbonate such as chalk.

In some cases, the amorphous solid may consist essentially of, or consist of a gelling agent, an aerosol generating agent, a tobacco material or a nicotine source, water, and optionally a flavour.

In the examples above, the source of aerosol generating medium 110 may have a base or coating or the like, which is substantially impermeable to aerosol. This arrangement may encourage the aerosol generated from heating of the source of aerosol generating medium 110 to flow away from the heater 120 and towards a mouthpiece or outlet of the device 100. This can help reduce the likelihood of condensation of aerosol within the device 100 and, as mentioned above, therefore increases both the cleanliness and lifetime of the device 100. The base may be formed of at least one of materials such as paper, cardboard, wood, pulp, plastic, ceramic, tobacco or a nicotine containing substance.

Thus there has been described an aerosol provision device comprising: a source of aerosol generating medium; and a heater; wherein the heater is configured to heat the aerosol generating medium to form an aerosol; wherein the source is configured to move within the device between a stowed position away (remote) from the heater and an aerosol generating position in which the source of aerosol generating medium is in contact with the heater.

The aerosol provision system may be used in a tobacco industry product, for example a non-combustible aerosol provision system.

In one embodiment, the tobacco industry product comprises one or more components of a non-combustible aerosol provision system, such as a heater and an aerosolizable substrate.

In one embodiment, the aerosol provision system is an electronic cigarette also known as a vaping device.

In one embodiment the electronic cigarette comprises a heater, a power supply capable of supplying power to the heater, an aerosolizable substrate such as a liquid or gel, a housing and optionally a mouthpiece.

In one embodiment the aerosolizable substrate is contained in or on a substrate container. In one embodiment the substrate container is combined with or comprises the heater. In one embodiment, the tobacco industry product is a heating product which releases one or more compounds by heating, but not burning, a substrate material. The substrate material is an aerosolizable material which may be for example tobacco or other non-tobacco products, which may or may not contain nicotine. In one embodiment, the heating device product is a tobacco heating product.

In one embodiment, the heating product is an electronic device.

In one embodiment, the tobacco heating product comprises a heater, a power supply capable of supplying power to the heater, an aerosolizable substrate such as a solid or gel material.

In one embodiment the heating product is a non-electronic article.

In one embodiment the heating product comprises an aerosolizable substrate such as a solid or gel material, and a heat source which is capable of supplying heat energy to the aerosolizable substrate without any electronic means, such as by burning a combustion material, such as charcoal.

In one embodiment the heating product also comprises a filter capable of filtering the aerosol generated by heating the aerosolizable substrate.

In some embodiments the aerosolizable substrate material may comprise an aerosol or aerosol generating agent or a humectant, such as glycerol, propylene glycol, triacetin or diethylene glycol.

In one embodiment, the tobacco industry product is a hybrid system to generate aerosol by heating, but not burning, a combination of substrate materials. The substrate materials may comprise for example solid, liquid or gel which may or may not contain nicotine. In one embodiment, the hybrid system comprises a liquid or gel substrate and a solid substrate. The solid substrate may be for example tobacco or other non-tobacco products, which may or may not contain nicotine. In one embodiment, the hybrid system comprises a liquid or gel substrate and tobacco.

In order to address various issues and advance the art, the entirety of this disclosure shows by way of illustration various embodiments in which the disclosure may be practiced and provide for a superior electronic aerosol provision system. The advantages and features of the disclosure are of a representative sample of embodiments only, and are not exhaustive or exclusive. They are presented only to assist in understanding and teach the claimed features. It is to be understood that advantages, embodiments, examples, functions, features, structures, or other aspects of the disclosure are not to be considered limitations on the disclosure as defined by the claims or limitations on equivalents to the claims, and that other embodiments may be utilised and modifications may be made without departing from the scope or spirit of the disclosure. Various embodiments may suitably comprise, consist of, or consist essentially of, various combinations of the disclosed elements, components, features, parts, steps, means, etc. In addition, the disclosure includes other embodiments not presently claimed, but which may be claimed in future.

The invention claimed is:
1. An aerosol provision system comprising:
aerosol generating medium;
a source of energy for heating, wherein the source of energy for heating is configured to cause heating of the aerosol generating medium to form an aerosol; and a housing configured to house the aerosol generating medium and in which the source of energy for heating is located, the housing further comprising a protected region for protecting the source of energy for heating;

wherein the source of energy for heating is configured to move within the system between an aerosol generating position proximate to the aerosol generating medium and a stowed position in which the source of energy for heating is in the protected region.

2. The aerosol provision system according to claim 1, wherein the protected region is at least one of a recess, opening, corridor, through-hole, groove or cavity within the housing.

3. The aerosol provision system according to claim 1, wherein:
the housing further comprises a protecting structure in which the protected region is located, or
the device further comprises a preventing element arranged to prevent, in use, the aerosol generating medium from entering the protected region.

4. The aerosol provision system according to claim 1, wherein the protected region has at least one opening through which the source of energy for heating is arranged to move as the source of energy for heating moves from the aerosol generating position to the stowed position,
the at least one opening having an area of less than 1.5 cm$^2$, less than 1.2 cm$^2$ or less than 1.0 cm$^2$.

5. The aerosol provision system according to claim 1, wherein the protected region is located between 0.5 to 2.0 cm from the aerosol generating position.

6. The aerosol provision system according to claim 1, wherein the protected region is arranged substantially further from an outer surface of the housing than the aerosol generating position.

7. The aerosol provision system according to claim 1, wherein the source of energy for heating is arranged to transfer heat to the aerosol generating medium via at least one of conductive heating, radiative heating and convective heating.

8. The aerosol provision system according to claim 1, further comprising a cover for covering a cover opening to the device, the cover configured to move between a closed position for covering the cover opening and an open position for providing a user access to the device through the cover opening, arranged such that the source of energy for heating is in the stowed position as the cover is moved towards the open position.

9. The aerosol provision system according to claim 8, further comprising an override system arranged to enable the cover to be in the open position and the source of energy for heating to be in the aerosol generating position simultaneously.

10. The aerosol provision system according to claim 8, wherein the cover is formed from the aerosol forming material.

11. The aerosol provision system according to claim 8, wherein the source of energy for heating is of a size to pass through the cover opening.

12. A method of generating an aerosol in an aerosol provision device, the method comprising:

providing aerosol generating medium;

providing a source of energy for heating;

providing a housing with a protected region;

moving the source of energy for heating from a stowed position in which the source of energy for heating is located in the protected region to an aerosol generating position in which the source of energy for heating is located proximate to the aerosol generating medium; and heating the aerosol generating medium to form an aerosol.

13. The method according to claim 12, moving the source of energy for heating from the aerosol generating position to the stowed position.

14. The method according to claim 12, further comprising deactivating the source of energy for heating prior to moving the source of energy for heating to the stowed position.

15. An aerosol provision device configured to receive aerosol generating medium, comprising:

a source of energy for heating, wherein the source of energy for heating is configured to, in use, cause heating of the aerosol generating medium to form an aerosol; and a housing for housing, in use, the aerosol generating medium and in which the source of energy for heating is located, the housing further comprising a protected region for protecting the source of energy for heating;

wherein the source of energy for heating is configured to, in use, move within the device between an aerosol generating position proximate to the aerosol generating medium and a stowed position in which the source of energy for heating is in the protected region.

16. The aerosol provision device according to claim 15, wherein the protected region is at least one of a recess, opening, corridor, through-hole, groove or cavity within the housing.

17. The aerosol provision device according to claim 15, wherein:

the housing further comprises a protecting structure in which the protected region is located, or the device further comprises a preventing element arranged to prevent, in use, the aerosol generating medium from entering the protected region.

18. The aerosol provision device according to claim 15, wherein the protected region has at least one opening through which the source of energy for heating is arranged to move as the source of energy for heating moves from the aerosol generating position to the stowed position, the at least one opening having an area of less than 1.5 $cm^2$, less than 1.2 $cm^2$ or less than 1.0 $cm^2$.

19. The aerosol provision device according to claim 15, wherein the protected region is located between 0.5 to 2.0 cm from the aerosol generating position.

20. The aerosol provision device according to claim 15, wherein the protected region is arranged substantially further from an outer surface of the housing than the aerosol generating position.

21. The aerosol provision device according to claim 15, further comprising a cover for covering a cover opening to the device, the cover configured to move between a closed position for covering the cover opening and an open position for providing a user access to the device through the cover opening, arranged such that the source of energy for heating is in the stowed position as the cover is moved towards the open position.

22. The aerosol provision device according to claim 21, further comprising an override system arranged to enable the cover to be in the open position and the source of energy for heating to be in the aerosol generating position simultaneously.

23. The aerosol provision device according to claim 21, wherein the cover is formed from the aerosol forming material.

24. The aerosol provision device according to claim 21, wherein the source of energy for heating is of a size to pass through the cover opening.

\* \* \* \* \*